United States Patent [19]

Gavin

[11] 4,359,905

[45] Nov. 23, 1982

[54] WEDGES FOR ULTRASONIC INSPECTION

[75] Inventor: Donald A. Gavin, Rexford, N.Y.

[73] Assignee: The United States of America as represented by the United States Department of Energy, Washington, D.C.

[21] Appl. No.: 211,591

[22] Filed: Dec. 1, 1980

[51] Int. Cl.³ .............. G01N 29/04; G01N 24/00; G01N 29/00

[52] U.S. Cl. .............................. 73/644; 73/623; 73/640; 310/335

[58] Field of Search ........... 73/640, 644, 642, 623, 73/784, 639; 310/335, 336, 338

[56]  References Cited

U.S. PATENT DOCUMENTS

| 3,350,923 | 11/1967 | Cross | 73/644 |
| 3,745,813 | 7/1973 | Uozumi | 73/644 |
| 4,127,788 | 11/1978 | Daugherty | 310/338 |
| 4,217,782 | 8/1980 | Pont | 73/637 |

FOREIGN PATENT DOCUMENTS 1285715  8/1972  United Kingdom ............ 73/642

Primary Examiner—Edward R. Kazenske
Assistant Examiner—David V. Carlson

[57] ABSTRACT

An ultrasonic transducer device is provided which is used in ultrasonic inspection of the material surrounding a threaded hole and which comprises a wedge of plastic or the like including a curved threaded surface adapted to be screwed into the threaded hole and a generally planar surface on which a conventional ultrasonic transducer is mounted. The plastic wedge can be rotated within the threaded hole to inspect for flaws in the material surrounding the threaded hole.

3 Claims, 5 Drawing Figures

WEDGES FOR ULTRASONIC INSPECTION

FIELD OF THE INVENTION

The present invention relates to ultrasonic transducers for flaw detection and more particularly, to an ultrasonic transducer capable of performing ultrasonic inspections of the material surrounding threaded holes.

BACKGROUND OF THE INVENTION

Non-destructive ultrasonic flaw inspection is a well developed art and numerous devices have been designed for this purpose. Some examples of such ultrasonic inspection devices are those disclosed in U.S. Pat. Nos. 3,350,923 (Cross); 3,745,813 (Uozumi); 3,763,694 (Rathburn et al) and 3,798,961 (Flambard et al).

A serious problem associated with most conventional ultrasonic inspection devices is that these devices require a smooth test surface in order to be effective. In fact, it is understood that one of the basic requirements in all military specifications and codes is that ultrasonic tests shall be performed on smooth surfaces. This limitation presents obvious difficulties in attempting to locate material flaws in regions of maximum thermal stress in test objects having threaded holes therein in that the maximum thermal stress regions are located adjacent to the threaded holes and cannot be reached using conventional methods which require smooth surfaces to carry out the ultrasonic inspection.

SUMMARY OF THE INVENTION

In accordance with the invention, an ultrasonic inspection apparatus is provided which enables material evaluation in regions which have generally been considered to be inaccessible for ultrasonic tests. In accordance with the invention, a mounting wedge is provided which includes a threaded surface adapted to permit the wedge to be screwed into the threaded hole under inspection and a generally planar surface on which a conventional ultrasonic transducer is mounted. Rotation of the wedge within the threaded hole varies the orientation of the transducer and permits flaw inspection in the material surrounding the hole. In a preferred embodiment, the wedge is in the shape of a one-half cylinder and the threaded surface of the wedge is a semicircle in cross section.

Other features and advantages of the invention will be set forth in, or apparent from, the detailed description of the preferred embodiments which follows.

DESCRIPTION OF A PREFERRED EMBODIMENT

Figure 1:
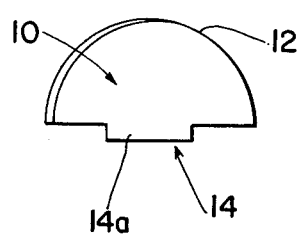
FIG. 1 is a plan view of an ultrasonic transducer mounting wedge constructed in accordance with a preferred embodiment of the invention.
Figure 2:
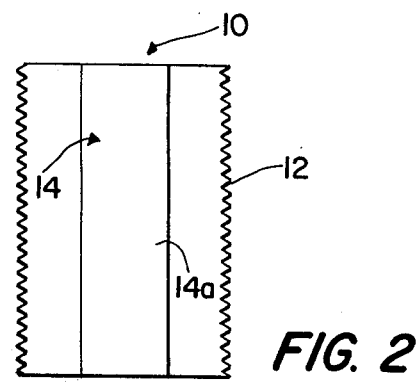
FIG. 2 is a side elevational view of one side of the wedge of FIG. 1.
Figure 3:
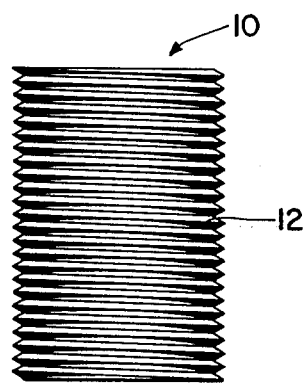
FIG. 3 is a side elevational view of the other side of the wedge of FIG. 1.
Figure 4:
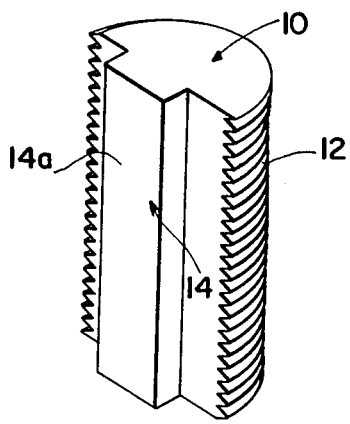
FIG. 4 is a perspective view of the wedge of FIG. 1.

Referring to FIGS. 1 to 4, a mounting wedge is shown for use in mounting an ultrasonic transducer so as to enable ultrasonic inspection of the material surrounding a threaded hole. The wedge, which is generally denoted 10, includes a first, curved, generally semicircular threaded surface 12 and a second, opposed, transducer mounting surface 14. The threaded surface 12 is threaded so as to be able to be screwed into a correspondingly threaded hole and it will be appreciated that different sized wedges having different thread patterns can be used depending on the characteristics of the threaded hole to be inspected. It will be understood that the threading of surface 12 is matched to that of the threaded hole. The transducer mounting surface includes a central ridge 14a which assists in mounting an ultrasonic transducer. More particularly, the ultrasonic transducer, which is a standard commercial item and is not shown in FIGS. 1 to 4, moves up and down in the threaded hole in which the wedge 10 is mounted, along ridge 14a, while scanning for defects along the axial length of the threaded hole. A short rod (not shown) is used to enable an operator to move the transducer up and down. If the threaded hole is large enough, the transducer is simply held against the flat surface of wedge 10 and moved manually. In a specific example, the transducer can be a right cylinder, one-half inch in diameter and height. Wedge 10 is fabricated of a plastic such as "Lucite" in a preferred embodiment although other materials may also be used.

Figure 5:
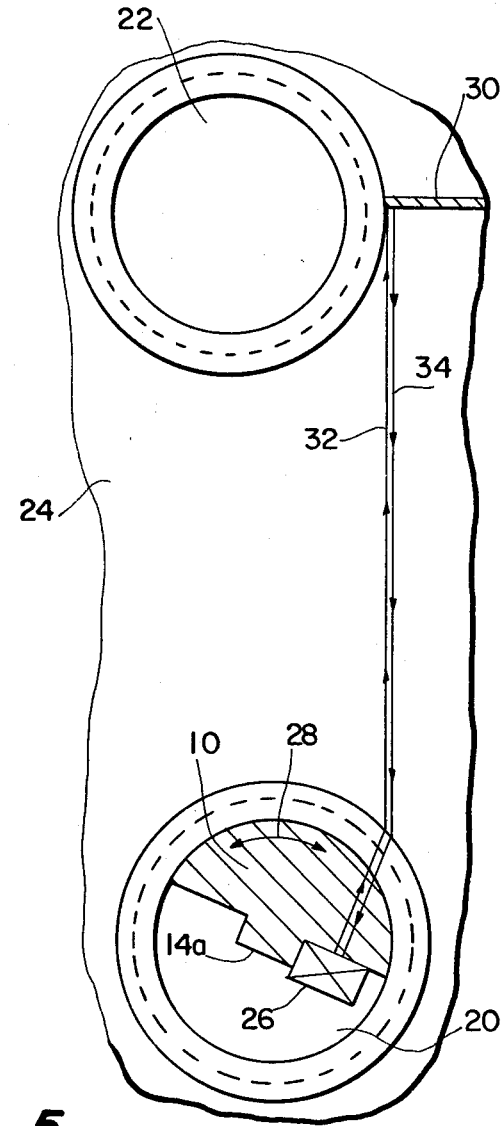
FIG. 5 is a plan view illustrating a use of the wedge of FIG. 1 in combination with an ultrasonic transducer in inspecting the material surrounding a threaded hole.

Referring to FIG. 5, the transducer mounting wedge 10 is shown in use in test set-up wherein a pair of tapped lifting holes 20 and 22 are formed in mock-up block 24. The wedge 10 has an ultrasonic transducer 26 mounted thereon on surface 14 and wedge 10 is threaded into tapped hole 20, as shown. The solid and dashed lines are used in FIG. 5 to indicate that hole 22 is tapped or threaded rather than smooth bore. Wedge 10 can be rotated in hole 20 as indicated by the double headed arrow denoted 28. A calibration notch 30 is located adjacent tapped hole 22 and, as indicated by the sound paths denoted 32 and 34, the sound wave transmitted by transducer 26 is refracted or bent around the tapped hole 20 to inspect a tapped hole 22 for possible flaws. The notch 30 represents an axial crack, typical of one kind of flaw to be detected. Sound path 32 corresponds to the refracted shear wave beam from transducer 26 and while sound path 34 corresponds to the reflected shear wave beam from the notch 30 back to transducer 26. Any standard ultrasonic testing unit can be used to process the output of transducer 26. A specific example of a unit which has been tested successfully is the Krautkramer Branson testing unit Model VSIP-11.

Although two tapped holes 20 and 22 are shown, it should be understood that the transducer 26 can be used to inspect the hole in which the transducer is disposed for flaws located circumferentially about that hole. The transducer is also used to inspect adjacent holes (hole 22) for radial flaws.

Several modifications can be made to the mounting wedge of the invention to vary the ultrasonic inspection with respect to either direction or mode of propagation. In particular, parameters such as the distance of the transducer from the center of a threaded hole, the radius of the threaded hole, the amount of bending or refraction of the sound wave, and the refractive index of the wedge material for the ultrasonic longitudinal waves and ultrasonic shear waves in steel or other materials, can be varied to better adapt the transducer system in the type of inspection required.

Although the invention has been described in relation to exemplary embodiments thereof, it will be understood by those skilled in the art that variations and modifications can be effected in these exemplary embodiments without departing from the scope and spirit of the invention.

I claim:

1. For use in performing an ultrasonic inspection of the material surrounding a threaded opening in a test device, an ultrasonic inspection apparatus comprising a wedge-like mounting member having a first, threaded surface which is adapted to be screwed into the threaded hole in the test object and a second, mounting surface; and an ultrasonic transducer mounted on said mounting surface, said mounting member being approximately semicircular in cross section and of a size such as to fit within the threaded hole in the test object and to leave space in said threaded hole for said ultrasonic transducer so as to enable rotation of said mounting member within said threaded hole and thus permit the orientation of said ultrasonic transducer relative to the threaded hole to be varied.

2. An apparatus as claimed in claim 1 wherein said mounting surface is generally planar and includes a central ridge.

3. An apparatus as claimed in claim 1 wherein said mounting member is in the shape of a half cylinder.

* * * * *